United States Patent [19]

Ishikawa et al.

[11] 4,276,295
[45] Jun. 30, 1981

[54] 3-AROMATIC MOIETY SUBSTITUTED-4(3H)-QUINAZOLINONES, PROCESS FOR PRODUCTION THEREOF, AND USE THEREOF

[75] Inventors: Masayuki Ishikawa, 14-13, Akazutsumi 3-chome, Setagaya-ku, Tokyo, Japan, 156; Hiromichi Tanaka, Yokohama, Japan; Yukuo Eguchi, Chiba, Japan; Shigeru Ito, Nagareyama, Japan; Yoshimi Takashima, Akishima, Japan; Masahiko Kobayashi, Kokubunji, Japan

[73] Assignee: Masayuki Ishikawa, Tokyo, Japan

[21] Appl. No.: 103,841

[22] Filed: Dec. 14, 1979

[30] Foreign Application Priority Data

Dec. 19, 1978 [JP] Japan ................................. 53-155764
Oct. 3, 1979 [JP] Japan ................................. 54-126738
Oct. 18, 1979 [JP] Japan ................................. 54-133582
Nov. 5, 1979 [JP] Japan ................................. 54-141987

[51] Int. Cl.³ .................. A61K 31/505; C07D 239/90
[52] U.S. Cl. ........................................ 424/251; 544/92; 544/284; 544/287; 560/103; 562/458
[58] Field of Search .................. 544/287, 284; 424/251

[56] References Cited

U.S. PATENT DOCUMENTS 3,047,462  7/1962  Maillard et al. ............... 544/284
3,721,671  3/1973  Yamamoto et al. ........... 544/284

FOREIGN PATENT DOCUMENTS 2329815  1/1974  Fed. Rep. of Germany .

OTHER PUBLICATIONS

Eguchi, et al., "Synthetic Studies of Antiatherogenic Agent (VII) Syntheses of Methylcarbamate of Substituted Quinazolinones", Reports of the Institute for Medical and Dental Engineering, vol. 11, 1977, pp. 56–59.

*Primary Examiner*—Anton H. Sutto
*Assistant Examiner*—James H. Turnipseed
*Attorney, Agent, or Firm*—Sherman & Shalloway

[57] ABSTRACT

Novel 3-aromatic moiety substituted-4(3H)-quinazolinone derivatives useful as a vasodilators, hypotensive and antiatherosclerotic agents having the formula of

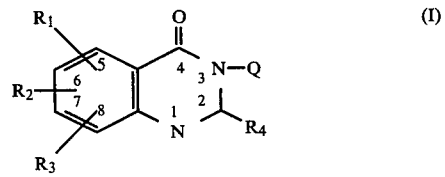

wherein $R_1$, $R_2$, $R_3$, $R_4$ and Q are as defined in the accompanying specification or its acid addition salt; and a process for producing the same.

14 Claims, No Drawings

3-AROMATIC MOIETY SUBSTITUTED-4(3H)-QUINAZOLINONES, PROCESS FOR PRODUCTION THEREOF, AND USE THEREOF

This invention relates to novel 3-aromatic moiety substituted-4(3H)-quinazolinone derivatives useful as vasodilators, hypotensive and antiatherosclerotic agents for the treatment of ischemic heart diseases, ischemic cerebral diseases, hypertension and atherosclerosis.

More specifically, this invention relates to 3-aromatic moiety substituted-4(3H)-quinazolinones of the formula

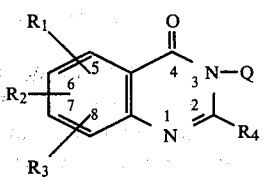

wherein $R_1$ and $R_3$ represent lower alkyl groups and $R_2$ represents a linear or branched lower alkoxycarbonyl group in which $R_1$, $R_2$ and $R_3$ are located at the 5-, 6- and 7-positions or at the 6-, 7- and 8-positions in this order;

$R_4$ represents a member selected from the group consisting of a hydrogen atom, linear or branched alkyl groups, monohalogenomethyl groups, trihalogenomethyl groups, an acetoxymethyl group and a hydroxymethyl group;

Q represents a group of the formula

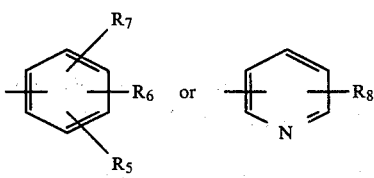

in which $R_5$ represents a member selected from the group consisting of a hydrogen atom, halogen atoms, lower alkyl groups and lower alkoxy groups, $R_6$ represents a member selected from the group consisting of a hydrogen atom, halogen atoms, lower alkyl groups, lower alkoxy groups, a trifluoromethyl group and a nitro group, $R_5$ and $R_6$ may together represent a methylenedioxy group when they are located on adjacent carbon atoms on the nucleus, $R_7$ represents a member selected from the group consisting of a hydrogen atom, halogen atoms, lower alkyl groups, lower alkoxy groups, a trifluoromethyl group, a nitro group, a cyano group, a hydroxyl group, lower alkanoyl groups, a carboxyl group, lower alkoxycarbonyl groups, a hydroxymethyl group, a carboxymethyl group, lower alkoxycarbonylmethyl group, an amino group, di-lower alkylamino groups, and (di-lower alkylamino) lower alkyl groups, and $R_8$ represents a hydrogen atom or a lower alkyl group; and when $R_4$ represents a methyl group, and when $R_1$, $R_2$ and $R_3$ are located at the 6-, 7- and 8-positions in this order and $R_4$ represents a hydroxymethyl group, $R_5$, $R_6$ and $R_7$ do not simultaneously represent a hydrogen atom; and acid addition salts thereof.

This invention also relates to a process for producing the aforesaid novel compounds and the use of them as vasodilators, hypotensive and antiatherosclerotic agents.

Heretofore, 4-hydroxymethyl-substituted and other 4-substituted derivatives of 7-alkoxycarbonyl-6,8-dialkyl-1-phthalazones have been known as compounds which exhibit such pharmacological properties as the ability to prevent thrombosis and arterosclerosis (U.S. Pat. No. 3,963,716). Methaqualone [2-methyl-3-(o-tolyl)-4(3H)-quinazolinone], a 3-phenyl-4(3H)-quinazolinone derivative, is known as a sedative and a hypnotic agent [see, Klosa, J. Prakt. Chem. 14, 84 (1961)].

The present inventors have now found that the 3-aromatic moiety substituted-4(3H)-quinazolinones of formula (I) and the acid addition salts thereof which are not described in the literature can be easily synthesized, and have low toxicity and superior pharmacological activities as vasodilating, hypotensive, spasmolytic and antiatherosclerotic agents, compared with the prior art. It has now been found that the compounds of the present invention have efficient vasodilating and spasmolytic effect on blood vessels such as coronary artery and cerebral artery. The tone of the smooth muscle of the blood vessels is also greatly reduced. In accord with the vasodilating effect, the compounds of the present invention are also effective to lower and normalize elevated blood pressure in a blood pressure lowering test using spontaneously hypertensive rats. In addition, in a test for experimental atherosclerosis induced by cholesterol feeding, the compounds of the present invention are found to be highly active in preventing atherosclerosis and in inhibiting cholesterol deposition on the arterial wall. These pharmacological effects complement one another and the compounds of the present invention are thus highly desirable as pharmaceutical agents to be used in the treatment of ischemic diseases such as angina pectoris, heart infarction and cerebral infarction, hypertensive diseases and atherosclerotic diseases.

It is an object of this invention therefore to provide the novel 3-aromatic moiety substituted-4-quinazolinones of formula (I) and the acid addition salts thereof.

Another object of this invention is to provide a process for producing the compounds of formula (I).

Still another object of this invention is to provide a vasodilating, hypotensive and antiatherosclerotic agent comprising the compound of formula (I) as an active ingredient, which is useful for the treatment of ischemic disorders, hypertension, atherosclerosis and the like.

The above and other objects and advantages of this invention will become more apparent from the following description.

The compounds of this invention are expressed by the following formula

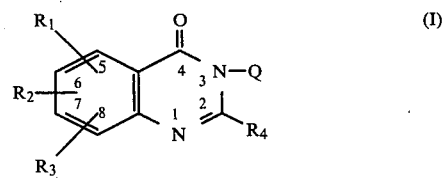

In formula (I), $R_1$ and $R_3$ represent a lower alkyl group, preferably a $C_1$-$C_4$ alkyl group such as a methyl group, and $R_2$ represents a linear or branched lower alkoxycarbonyl group preferably a $C_1$-$C_4$ alkoxycarbonyl group, in which $R_1$, $R_2$ and $R_3$ are located at the 5-, 6- and 7-positions or at the 6-, 7- and 8-positions in this order; $R_4$ represents a member selected from the group consisting of a hydrogen atom, linear or branched alkyl groups, preferably $C_1$-$C_6$ alkyl groups, monohalogenomethyl groups, trihalogenomethyl groups, an acetoxymethyl group and a hydroxymethyl group; Q represents a group of the formula

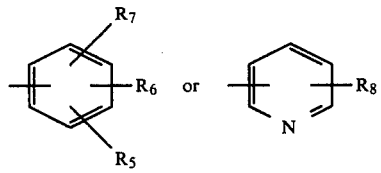

in which $R_5$ represents a member selected from the group consisting of a hydrogen atom, halogen atoms, lower alkyl groups, preferably $C_1$-$C_4$ alkyl groups and lower alkoxy groups, preferably $C_1$-$C_4$ alkoxy groups, $R_6$ represents a member selected from the group consisting of a hydrogen atom, halogen atoms, lower alkyl groups, preferably $C_1$-$C_4$ alkyl groups, lower alkoxy groups, preferably $C_1$-$C_4$ alkoxy groups, a trifluoromethyl group and a nitro group, $R_5$ and $R_6$ may together form a methylenedioxy group when they are located on adjacent carbon atoms of the nucleus, $R_7$ represents a member selected from the group consisting of a hydrogen atom, halogen atoms, lower alkyl groups, preferably $C_1$-$C_4$ alkyl groups, lower alkoxy groups, preferably $C_1$-$C_4$ alkoxy groups, a trifluoromethyl group, a nitro group, a cyano group, a hydroxyl group, lower alkanoyl groups, preferably $C_1$-$C_4$ alkanoyl groups such as an acetyl group, a carboxyl group, lower alkoxycarbonyl groups, preferably $C_1$-$C_4$ alkoxycarbonyl groups, a hydroxymethyl group, a carboxymethyl group, lower alkoxycarbonylmethyl groups, preferably $C_1$-$C_4$ alkoxycarbonylmethyl groups, amino groups, di-lower alkyl amino groups, preferably di($C_1$-$C_4$ alkyl)amino groups, and (di-lower alkyl amino)-lower alkyl groups preferably [di($C_1$-$C_4$ alkyl)amino]($C_1$-$C_4$)alkyl groups and $R_8$ represents a hydrogen atom or a lower alkyl group, preferably a $C_1$-$C_4$ alkyl group; when $R_4$ represents a methyl group and when $R_1$, $R_2$ and $R_3$ are located at the 6-, 7- and 8-positions in this order and $R_4$ is a hydroxymethyl group, $R_5$, $R_6$ and $R_7$ do not simultaneously represent a hydrogen atom.

The compound of formula (I) or its acid addition salt can be produced by reacting a compound of the following formula

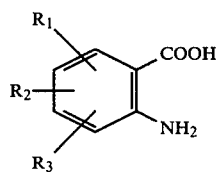

wherein $R_1$, $R_2$ and $R_3$ are as defined above with regard to formula (I), with a compound of the formula

wherein $R_4$ is as defined above with regard to formula (I), and X represents a halogen atom or a group of the formula

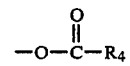

in which when $R_4$ is hydrogen, X may be a hydroxy group or an acetoxy group, and then reacting the product with a compound of the formula $$Q-NH_2 \quad (IV)$$

wherein Q is as defined above with regard to formula (I);

or converting the group —COOH of the compound of formula (II) into its reactive derivative, then reacting the product with the compound of formula (IV), and then reacting the product wth the compound of formula (III); and optionally hydrolyzing or reducing the reaction product, and if desired, treating the product with an acid, preferably a pharmaceutically acceptable acid to convert it into an acid addition salt.

A compound of formula (I) in which $R_4$ is a hydrogen, which is expressed by the following formula

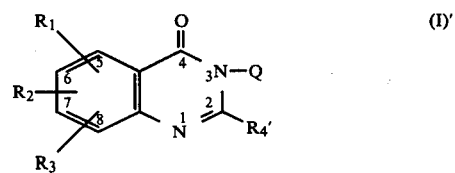

wherein $R_1$, $R_2$, $R_3$ and Q are as defined above with regard to formula (I), and $R'_4$ represents a hydrogen atom, or its acid addition salt may also be produced by reacting a compound of the following formula

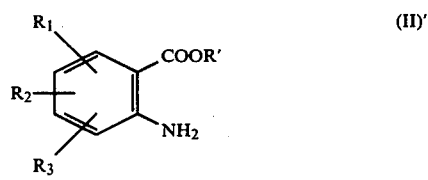

wherein $R_1$, $R_2$ and $R_3$ are as defined above with regard to formula (I), and R' represents a hydrogen atom or a lower alkyl group, with a compound of the following formula $$Q-N=CH-NH-Q \quad (V)$$

wherein Q is as defined above with regard to formula (I);

and optionally hydrolyzing or reducing the reaction product, and if desired, treating the product with an acid, preferably a pharmaceutically acceptable acid to convert it into an acid addition salt.

The production of the novel compounds of this invention can be schematically shown as follows.

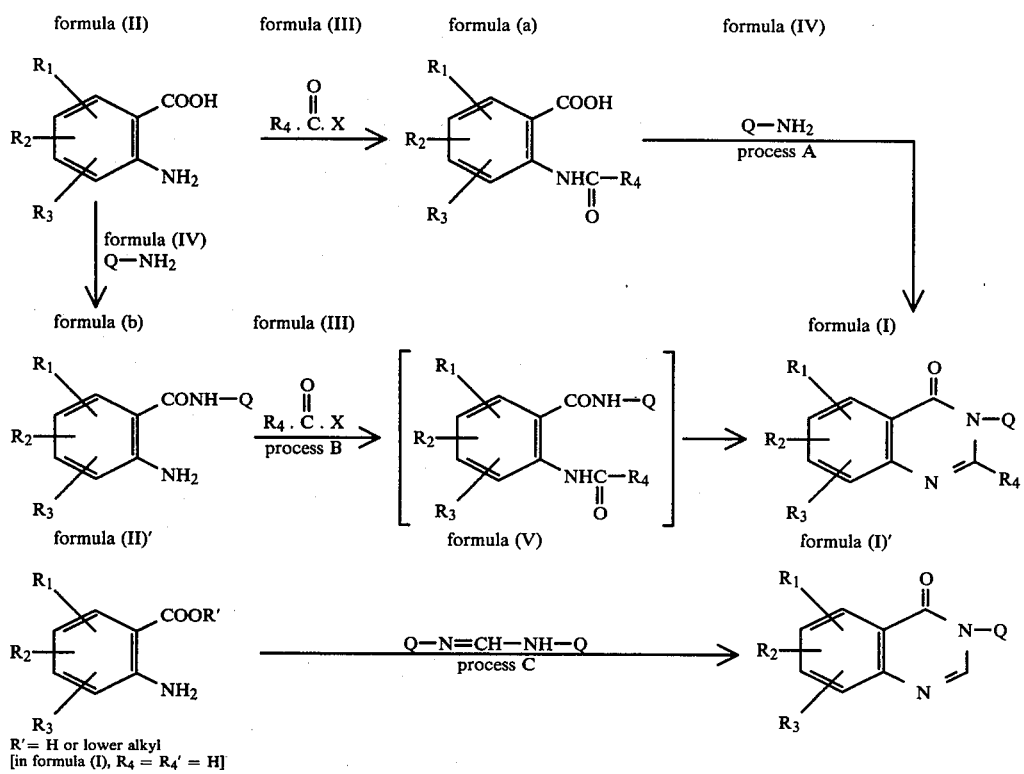

R' = H or lower alkyl
[in formula (I), R₄ = R₄' = H]

Specific embodiments of processes A, B and C are described in detail below.

In processes A and B, examples of the compound of formula (II) include 2-amino-5-ethoxycarbonyl-4,6-dimethylbenzoic acid, 2-amino-4,6-dimethyl-5-propoxycarbonylbenzoic acid, 2-amino-5-isopropoxycarbonyl-4,6-dimethylbenzoic acid, 2-amino-5-butoxycarbonyl-4,6-dimethylbenzoic acid, 2-amino-5-isobutoxycarbonyl-4,6-dimethylbenzoic acid, and 2-amino-4-ethoxycarbonyl-3,5-dimethylbenzoic acid, 2-amino-3,5-dimethyl-4-propoxycarbonylbenzoic acid, 2-amino-4-isopropoxycarbonyl-3,5-dimethylbenzoic acid, 2-amino-4-butoxycarbonyl-3,5-dimethylbenzoic acid, and 2-amino-4-isobutoxycarbonyl-3,5-dimethylbenzoic acid.

The compound of formula (II) can be produced by known means, for example by the Hoffmann rearrangement reaction of a 4-alkoxycarbonyl-3,5-dialkylphthalimide (see, Eguchi and Ishikawa, Report of Institute for Medical and Dental Engineering, Tokyo Medical and Dental University, Vol. 11, page 55, 1977), or the Curtius rearrangement reaction of a 2,4-dialkoxycarbonyl-3,5-dialkylbenzoic acid azide.

Examples of formula (III) in processes A and B include formic acid, formic acetic anhydride, acetic anhydride, propionic anhydride, isopropionic anhydride, n-butyric anhydride, isobutyric anhydride, valeric anhydride, isovaleric anhydride, trifluoroacetic anhydride and acetyl chloride, acetyl bromide, propionyl chloride, propionyl bromide, isopropionyl chloride, isopropionyl bromide, butyryl chloride, butyryl bromide, isobutyryl chloride, isobutyryl bromide, isovaleryl chloride, isovaleryl bromide, hexanoyl chloride, hexanoyl bromide, and trifluoroacetyl chloride.

Examples of the compound of formula (IV) in processes A and B include aniline, o-, m-, and p-chloroanilines, o-, m-, and p-bromoanilines, o-, m-, and p-fluoroaniline, o-, m-, and p-toluidine, o-, m-, and p-anisidine, 3,4-dimethoxyaniline, 3,4-methylenedioxyaniline, α,α,α-trifluoro-o-, -m- and -p-toluidine, p-, m-, and p-nitroaniline, o-, m-, and p-cyanoaniline, o-, m-, and p-aminophenyl, o-, m-, and p-aminobenzoic acids and their methyl-, ethyl-, n-propyl-, isopropyl, n-butyl-, isobutyl-, and t-butyl esters, o-, m-, and p-aminophenyl acetic acid and their methyl-, ethyl-, n-propyl-, isopropyl, n-butyl-, isobutyl- and t-butyl esters, o-, m-, and p-aminoacetophenone, N,N-dimethyl-o-, -m-, and -p-phenylenediamine, N,N-diethyl-o-, -m-, and-p-phenylenediamine, 2,4-dichloroaniline, 2,6-dichloroaniline, 2,3-, 2,4-, 2,5-, and 2,6-xylenes, 2,4,6-trimethylaniline, 3-chloro-2-methylaniline, 4-chloro-2-methylaniline, 5-chloro-2-methoxyaniline, 3-chloro-4-methylaniline, 4-hydroxy-2-methylaniline, 2-amino-4-nitrophenol, 2-amino-5-nitrophenol, 2-amino-4-chlorophenol, 2-amino-4-methylphenol, 4-amino-2-nitrophenol, 4-methoxy-2-nitroaniline, 2-methoxy-4-nitroaniline, 2-methoxy-5-nitroaniline, 2-bromo-4-methylaniline, 4-diethylamino-2-methoxyaniline, 2-chloro-4-(trifluoromethyl)aniline, 4-chloro-2-(trifluoromethyl)aniline, 2-nitro-4-(trifluoromethyl)-aniline, o-, m-, and p-(dimethylaminomethyl)aniline, o-, m-, and p-(diethylaminomethyl)aniline, 2-amino-, 3-amino-, and 4-aminopyridine, 3-amino-2-methylpyridine, and 3-amino-6-methylpyridine.

According to process A, the compound of formula (II) is reacted with the compound of formula (III) to acylate (or formylate) —NH₂ of the compound of formula (II), and then the resulting product is reacted with the amine of formula (IV).

When an acid halide is used as the compound (III) in an embodiment of acylation using the compound (III) in which R₄ is other than hydrogen, the reaction between the compound (II) and the compound (III) is carried out preferably in an inert organic solvent such as benzene or toluene in the presence of a dehydrohalogenating agent such as a base (e.g., pyridine). When an acid anhydride such as acetic anhydride is used as the compound (III), it is possible to use the anhydride in an excessive amount and to carry out the reaction in the absence of solvent thus causing the acid anhydride to act concurrently as a solvent. In this embodiment, the use of a base such as pyridine can be omitted. The acylation reaction proceeds even at room temperature, and the reaction temperature may, for example, be room temperature to about 150° C. The reaction time can be selected as required, and is, for example, about 1 hour to about 12 hours. The amount of the compound of formula (III) used in the acylation can be selected as required. For example, its amount is about 1 to 3 moles per mole of the compound (II). When it is desired to use it concurrently as a reaction solvent, the compound (II) can be used in larger amounts.

In the embodiment of acylation, the acylation product is obtained in the following formulae depending upon the reaction or working up conditions.

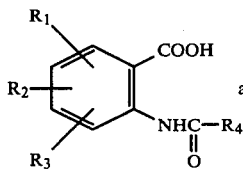
formula (a)

and/or

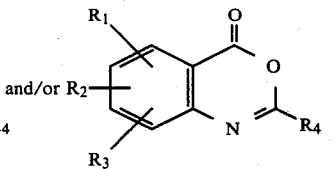
formula (a)'

Generally, when the reaction temperature is low or the finishing treatment of the reaction product is performed under acidic conditions, the N-acylated product of formula (a) is obtained as a main product. When the reaction temperature is high, the 3,1,4-benzoxane derivative of formula (a) is obtained as a main product. It is not important however which of the compounds is obtained as a main product in the acylation reaction. The compound of formula (a), the compound of formula (a)' or a mixture of these compounds, when subsequently condensed with the compound of formula (IV), gives the desired product of formula (I) in good yields. The resulting acylation reaction product can be reacted with the compound of formula (IV) after isolation and purification. This is not essential, and the reaction mixture obtained after the acylation reaction may be directly reacted with the compound of formula (IV), thus giving operating advantage.

The condensation reaction between the resulting acylation product and the amine of formula Q—NH$_2$ can be performed in an inert organic solvent such as toluene and xylene in the presence of a conventional condensing agent. Examples of the condensing agent are phosphorus trichloride, hydrogen chloride and polyphosphoric acid. The amount of the condensing agent can be properly selected, and may, for example, be about 0.3 to about 10 moles per mole of the reaction product of formula (a) and/or (a)'. The amount of the compound (IV) can be suitably selected, and may, for example, be about 1 to about 3 moles per mole of the reaction product of formula (a) and/or (a)'.

The reaction between the reaction product of formula (a) and/or (a)' and the amine of formula (IV) is desirably carried out at elevated temperatures of, say, about 80° to about 150° C. The reaction time can be selected properly, and may, for example, be about 1 hour to about 5 hours.

Some specific examples of the embodiment involving the use of the compound of formula (III) in which R$_4$ is other than hydrogen are described below.

For example, when acetic anhydride is used as the compound (III), the process can be practised as follows:

The compound of formula (II) is dissolved in acetic anhydride, and the solution is boiled under reflux for 1 to 3 hours. Under reduced pressure, the excess of the acetic anhydride is distilled off, and the residue is worked up in a customary manner to afford the 3,1,4-benzoxanone derivative of formula (a)' in a yield of 80 to 95% (of theory). The resulting compound of formula (a)' is reacted with the compound of formula (IV) in the presence of a solvent such as toluene or xylene and a condensing agent, preferably phosphorus trichloride. Preferably, 1 to 2 moles of the compound of formula (IV) and 0.3 to 1.5 moles of phosphorus trichloride are used per mole of the compound of formula (a)'. The condensing reaction is preferably carried out by heating the materials for 2 to 5 hours at a temperature near the boiling point of the reaction mixture. The reaction mixture is worked up in a customary manner to afford the compound of formula (I) easily in a yield of 60 to 80% (of theory) based on the compound of formula (II).

When an acid chloride is used as the compound of formula (III), the process can be practised, for example, as shown below. The compound of formula (II) is dissolved in benzene or toluene, and pyridine is added in an amount of 5 to 30 moles or more per mole of the compound (II). Then, with stirring under ice cooling, 1 to 5 moles, especially 1.2 to 3 moles, per mole of the compound (II), of the acid chloride (III) is added dropwise. After the addition, the mixture was allowed to stand at room temperature for 12 to 24 hours, and worked up in a customary manner to afford the N-acylated compound of formula (a) in a yield of 60 to 90% (of theory) based on the compound (II). Condensation of the acylation product with the compound (IV) in the presence of phosphorus trichloride in the aforesaid manner gives the compound of formula (I) in a similar yield.

In the case of the compound of formula (I) in which R$_4$ is hydrogen, process A can be carried out, for example, in the following manner.

Formylation of the compound of formula (II) can be advantageously carried out by an analogous method described in Huffman, Journal of Organic Chemistry, Vol. 23, pages 727–730, 1958.

For example, about 1 to 3 moles, per mole of the compound (II), of formic acid is provided in a reactor. Then, acetic anhydride is added in an amount of about 2 to about 2.5 moles, for example, per mole of formic acid. The mixture of formic acid and acetic anhydride is heated, for example, to 50° to 60° C. with stirring. It is stirred for about 1 to about 2 hours at this temperature, and then cooled. About one mole of the compound of formula (II) is added while it is cooled with stirring. The mixture is reacted at room temperature for several hours. The reaction mixture is poured into water, and the precipitated crystals are collected by filtration. Or the reaction mixture is extracted with an organic solvent, and worked up in a customary manner. Thus, the N-formyl product of the compound (II) is obtained in a yield of, for example, 80 to 90%.

The formyl product obtained is reacted with the amine of formula (III) in a solvent such as toluene or xylene in the presence of a condensing agent preferably phosphorus trichloride. The suitable amount of the amine is about 1 to about 2 moles per mole of the formyl product, and the suitable amount of phosphorus trichloride is about 0.3 to about 1.5 moles per mole of the formyl product. The reaction is carried out preferably by heating the materials for 2 to 5 hours at a temperature near the boiling point of the solvent. Then, the reaction mixture is treated with cold water, made alkaline with sodium bicarbonate or sodium carbonate, extracted with an organic solvent, and worked up in a customary manner. The compound of formula (I) is thus obtained in a yield of, for example, 50 to 80% (of theory).

According to process B in this invention, the group —COOH of the compound of formula (II) is converted to its reactive derivative, and the resulting product is reacted first with the compound (IV) and then with the compound (III). In process B, the reaction of converting —COOH to its reactive derivative can be performed by using thionyl chloride. In this example, the compound (II) may be reacted with thionyl chloride in an inert organic solvent such as benzene. The amount of thionyl chloride is suitably about 2 to about 10 moles per mole of the compound (III). The reaction can be carried out by heating the materials under reflux for about 1 to about 5 hours at a temperature at which the reaction mixture gently boils. The solvent and the excess of thionyl chloride are distilled off from the reaction mixture. Without isolating and purifying the residue, it is dissolved in a solvent such as benzene, methylene chloride or chloroform, and about 1 to about 3 moles, per mole of the compound (II), of the amino compound of formula (IV) is added. The mixture is stirred at room temperature for about 2 to about 20 hours, or heated for several hours at a temperature of about 70° to 100° C., to afford the anilide derivative (b) of compound (II)

(b)

wherein $R_1$, $R_2$, $R_3$ and Q are as defined above, in a yield of, for example, 70 to 90% (of theory) based on the compound (II). Preferably after isolation and purification, the resulting compound of formula (b) is dissolved in a solvent such as glacial acetic acid, and the compound of formula (III), in which X is preferably a chlorine or bromine atom, is added in an amount of, for example, about 1 to about 5 moles per mole of the compound (b). The mixture is heated at a temperature of, say, about 100° to 150° C. for a period of about 1 to 5 hours. The reaction mixture is worked up in a customary manner to afford the compound of formula (I) in a yield of about 50 to about 80% (of theory) based on the compound (b).

When a compound of formula (III) in which $R_4$ is H is used, it is desirable to heat the materials together with a condensing agent such as phosphorus trichloride, hydrogen chloride or polyphosphoric acid at a temperature of about 100° to about 150° C. When phosphorus trichloride is used as the condensing agent, the reaction is preferably carried out in a solvent such as toluene.

Process B can be performed especially advantageously when $R_4$ represents a halogenomethyl group. By heating the compound of formula (I) in which $R_4$ is a chloromethyl group obtained by this process together with an alkali metal fluoride such as potassium fluoride at 150° to 180° C. for several hours in a solvent such as dimethylsulfoxide, dimethyl Cellosolve or ethylene glycol, the corresponding fluoromethyl derivative can be advantageously produced.

The compound (Ib) of formula (I) in which $R_4$ is a hydroxymethyl group can be produced by hydrolyzing a compound (Ia) of formula (I) in which $R_4$ is a halogenomethyl group. The hydrolysis can be performed in a customary manner directly by using an acid or alkali. Preferably, however, the halogenomethyl compound (Ia) is reacted with an alkali metal salt of an aliphatic carboxylic acid, preferably sodium acetate to form the corresponding alkanoyloxy compound (Ic), which is then hydrolyzed with an acid or alkali.

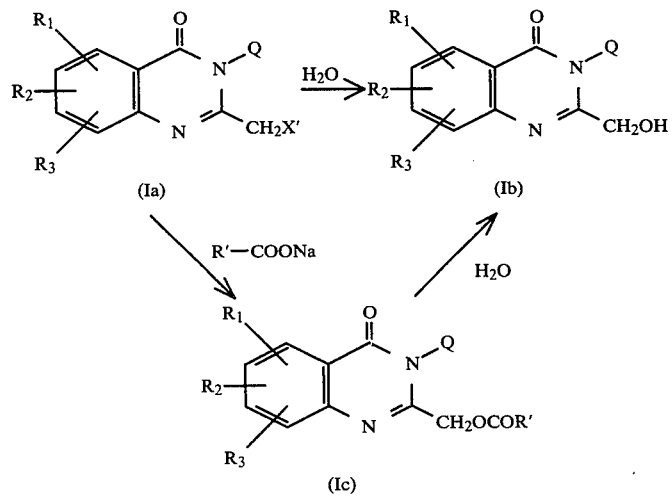

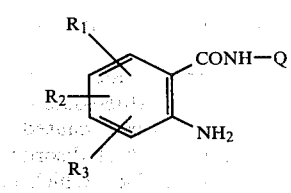

wherein $R_1$, $R_2$, $R_3$ and Q are as defined hereinabove, X' represents a halogen atom, and R' represents a lower alkyl group, preferably a methyl group.

In the embodiment of the hydrolysis, the procedure may, for example, be as follows: The compound (Ia) is dissolved in a solvent such as ethanol, dimethyl formamide or dimethylsulfoxide, and anhydrous sodium acetate is added in an amount of about 1 to about 3 moles. Preferably about 0.1 to about 0.5 moles, per mole of the compound (Ia), of sodium iodide or potassium iodide is preferably added to the mixture. The mixture is then heated at a temperature of about 50° to about 200° C., preferably about 100° to about 150° C., for about 1 to about 5 hours. The reaction mixture is worked up in a customary manner to afford the acetoxy product (Ic) in a yield of, for example, about 50 to about 80% (of theory). Hydrolysis of the acetoxy product with an acid or alkali in a customary manner gives the compound of formula (Ib) in a yield of about 50 to about 90% (of theory) based on the acetoxy product. Alternatively, the acetoxy product may be hydrolyzed directly with an acid or alkali without prior isolation and purification.

According to this invention, the compound of formula (I)′, which corresponds to formula (I) in which $R_4$ is a hydrogen atom,

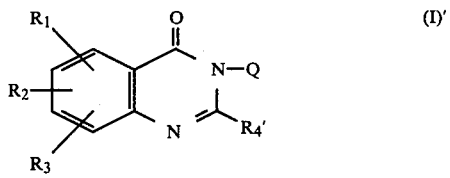

wherein $R_1$, $R_2$, $R_3$ and Q are as defined above with regard to formula (I), and $R'_4$ represents a hydrogen atom, can also be produced by process C.

According to process C, a compound of the following formula

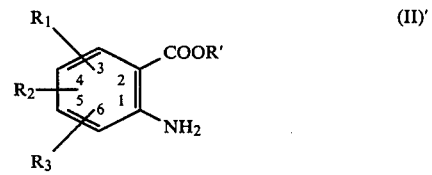

wherein $R_1$, $R_2$ and $R_3$ are as defined above with regard to formula (I), and R′ represents a hydrogen atom or lower alkyl group, is reacted with a compound of the formula $$Q-N=CH-NH-Q \qquad (V)$$

wherein Q is as defined above with regard to formula (I).

The compound of formula (II)′ may be produced by a known reaction similar to that described hereinabove with regard to compound (II). Examples of the compound of formula (II)′ include those of formula (II) in which R′ represents a lower alkyl group in addition to those of formula (II) in which R is H exemplified hereinabove. Specific examples include 4- or 5-ethoxycarbonyl-3,5 or 4,6-dimethyl-2-methoxycarbonylaniline, 4- or 5-propoxycarbonyl-3,5 or 4,6-dimethyl-2-methoxycarbonylaniline, 4- or 5-isopropoxycarbonyl-3,5 or 4,5-dimethyl-2-methoxycarbonylaniline, 4- or 5-butoxycarboxyl-3,5 or 4,6-dimethyl-2-methoxycarbonylaniline, 4- or 5-isobutoxycarbonyl-3,5 or 4,6-dimethyl-2-methoxycarbonyl-2,4 or 2,5-diethoxycarbonyl-3,5 or 4,6-dimethylaniline, 2-ethoxycarbonyl-4 or 5-propoxycarbonyl-3,5- or 4,6-dimethylaniline, 2-ethoxycarbonyl-4 or 5-isopropoxycarbonyl-3,5- or 4,6-dimethylaniline, 4- or 5-butoxycarbonyl-2-ethoxycarbonyl-3,5 or 4,6-dimethylaniline and 2-ethoxycarbonyl-4 or 5-isobutoxycarbonyl-3,5 or 4,6-dimethylaniline.

The compound of formula (V) can be produced by reacting the corresponding aniline derivative with an orthoformic acid ester (see Meyer and Wagner, Journal of the Organic Chemistry, Vol. 8, pages 239–252, 1943)

Examples of the compound of formula (V) include N,N-diphenylformamidine, N,N-di-(o-tolyl)-formamidine, N,N-di-(m-tolyl)-formamidine, N,N-di-(p-tolyl)-formamidine, N,N-di-(o-, m- or p-chlorophenyl)-formamidine, N,N-di-(o-, m-, or p-bromophenyl)-formamidine, N,N-di-(o-, m- or p-fluorophenyl)-formamidine, N,N-di-(o-, m- or p-methoxyphenyl)-formamidine, N,N-di-(o-, m- or p-ethoxyphenyl)-formamidine, N,N-di-(o-, m- or p-trifluorophenyl)-formamidine, N,N-di-(o-, m- or p-nitrophenyl)-formamidine, N,N-di-(2-methyl-4-methoxyphenyl)-formamidine, N,N-di-(2-methyl-4-ethoxyphenyl)-formamidine, N,N-di-(2,4-dimethylphenyl)-formamidine, N,N-di-(3,4-dimethylphenyl)-formamidine, N,N-di-(3,4-dimethoxyphenyl)-formamidine, N,N-di-(3,4-diethoxyphenyl)-formamidine, N,N-di-(3,4-methylenedioxyphenyl)-formamidine, N,N-di-(2,6-dichlorophenyl)-formamidine, N,N-di-(2,6-difluorophenyl)-formamidine, N,N-di-(2-methyl-3,4-dimethoxyphenyl)-formamidine, N,N-di-(2-methyl-3,4-diethoxyphenyl)-formamidine, N,N-di-(2-methyl-3,4-methylenedioxyphenyl)-formamidine, and N,N-di-(3,4,5-trimethoxyphenyl)-formamidine.

Process C can be performed, for example, by mixing the compound of formula (II)′ uniformly with about 1 to about 1.2 moles, per mole of the compound (II)′, of the compound (V) in an open reactor, and heating the mixture at about 150° to 250° C., preferably about 200° C., with stirring. The reaction time can be varied according to the type of the compound (V) and the reaction temperature. At a temperature of about 200° C., a period of about 1 to about 5 hours may be used. The reaction mixture is dissolved in a suitable organic solvent, and the by-product aniline derivative

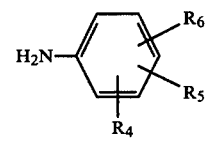

is removed, for example, by extraction with dilute hydrochloric acid. The organic solvent is distilled off, and the residue is separated and purified by an ordinary purifying method such as recrystallization or column chromatography. The yield of the final product is about 50 to about 80% of theory.

If desired, the compound of formula (I) can be converted to its acid addition salt, preferably its pharmaceutically acceptable acid addition salt. The formation of the acid addition salt can be effected by conventional general procedures. Example of acids that can be used to form such a salt include inorganic acids such as hydrochloric acid, sulfuric acid and hydrobromic acid and organic acids such as oxalic acid, maleic acid, malic acid and tartaric acid.

According to this invention, there is provided a vasodilating hypotensive and antiatherosclerotic agent useful for the treatment of diseases caused by ischemic heart disorder, ischemic cerebral disorder, hypertension, atherosclerosis and the like, which comprises a:

effective amount of the aromatic moiety substituted-4(3H)-quinazolinone of formula (I) or its pharmaceutically acceptable acid addition salt and a pharmaceutically acceptable liquid or solid diluent or carrier.

Examples of such pharmaceutically acceptable liquid or solid diluent or carrier include solid carriers such as sodium chloride, glucose, lactose, starch, sucrose, magnesium stearate, cetyl alcohol, cacao butter and spermaceti; and liquid carriers such as distilled water, isotonic sodium chloride solution, Ringer's solution, Locke's solution, polyethylene glycol, propylene glycol, ethyl alcohol, glycerol and vegetable oils.

The vasodilators of this invention may be in various formulations such as powders, granules, particles, tablets, capsules, troches, suspensions and solutions.

The dosage of the vasodilator of this invention is about 1 to about 100 mg/kg/day although it can be properly changed depending upon the type and extent of the patient's condition, the method of administration, etc.

The amount of the compound of formula (I) or its pharmaceutically acceptable acid addition salt to be included in the vasodilator of this invention can be properly changed according to the formulation of the vasodilator, the method of administration, etc. For example, it is about 1 to about 80% by weight based on the weight of the vasodilator.

Tests for pharmacological effects and for acute toxicity of several examples of the compounds of this invention are shown below under the headline "Test for blood vessel relaxing effect" and "Test for acute toxicity".

The following Examples illustrate the production of the compounds of this invention.

EXAMPLE 1

Acetic formic anhydride was prepared (but not isolated) by heating a mixture of 30 ml of acetic anhydride and 14.5 ml of 90% formic acid for two hours at 50°–60° C. To the mixture cooled to room temperature was added portionwise with stirring 15.0 g of 2-amino-5-ethoxy-carbonyl-4,6-dimethylbenzoic acid. Stirring was continued for another two hours and the mixture was poured into ice water. The resulting precipitates were filtered and air dried to yield 14.2 g of a crystalline solid. The solid so obtained was recrystallized from ethyl acetate/n-hexane to afford 11.7 g (69.8% of theory) of pure 2-formylamino-5-ethoxycarbonyl-4,6-dimethylbenzoic acid melting at 146.5°–147.5° C.

To a room temperature suspension of 1.06 g of the acid obtained above and 0.52 g of o-aminophenol in 30 ml of toluene was added dropwise with stirring a solution of 0.22 ml of phosphorous trichloride in 10 ml of toluene. The mixture was refluxed for 3 hours at 130° C. After the mixture had been cooled to room temperature, it was neutralized with saturated aqueous sodium carbonate solution, and the layers were separated. The aqueous layer was extracted with chloroform, and the combined organic extracts were washed with water, and dried over anhydrous sodium sulfate. The organic solvent was distilled off. The resulting residue was recrystallized from ethanol/n-hexane to yield 0.87 g (64.5% of theory) of 6-ethoxy-carbonyl-3-(2-hydroxyphenyl)-5,7-dimethyl-4(3H)-quinazolinone melting at 197°–198° C. $^1$H NMR: $\delta$(DMSO-d$_6$) 1.35 (t, 3H), 2,36 (s, 3H), 2.68 (s, 3H), 4.38 (q, 2H), 6.90- 7.50 (m, 5H), 8.05 (s, 1H), 9.90 (broad, 1H).

EXAMPLE 2

To 14.5 ml of 90% formic acid was added 30 ml of acetic anhydride. The mixture was warmed, and then heated to 50°–60° C. for two hours. To the mixture cooled to room temperature was added portionwise with stirring 15.0 g of 2-amino-4-ethoxycarbonyl-3,5-dimethylbenzoic acid. The mixture was further stirred at room temperature for 3 hours and poured into ice water. The resulting precipitate was filtered and recrystallized from ethyl acetate/n-hexane to yield 11.8 g (70.5% of theory) of 2-formylamino-4-ethoxycarbonyl-3,5-dimethylbenzoic acid melting at 144.5°–146° C.

To a room temperature suspension of 1.1 g of the acid obtained above and 0.7 g of ethyl o-aminobenzoate in 30 ml of toluene was added with stirring a solution of 0.3 ml of phosphorous trichloride in 10 ml of toluene. The mixture was refluxed for 3 hours at 130° C. After cooling, the mixture was neutralized with saturated aqueous sodium bicarbonate, and the layers were separated. The aqueous layer was extracted with chloroform, and the combined organic extracts were washed with water, and dried over anhydrous sodium sulfate. The organic solvent was distilled off. The resulting residue was recrystallized from ethanol/water to yield 1.01 g (62% of theory) of 7-ethoxycarbonyl-3-[2-(ethoxycarbonyl)-phenyl]-6,8-dimethyl-4(3H)-quinazolinone melting at 116°–117° C. $^1$H NMR: $\delta$(CDCl$_3$) 1.04 (t, 3H), 1.42 (t, 3H), 2.42 (s, 3H), 2.61 (s, 3H), 4.16 (q, 2H), 4.48 (q, 2H), 7.30–8.30 (m, 6H)

To a solution of 0.79 g of 7-ethoxycarbonyl-3-[2-(ethoxycarbonyl)phenyl]-4(3H)-quinazolinone described above in 50 ml of ethanol, was added a solution of 0.16 g of potassium hydroxide in 5 ml of water. The mixture was heated at 60° C. for 2 hours, diluted with water, and concentrated under reduced pressure. The concentrate was acidified with hydrochloric acid and extracted with chloroform. The extract was washed with water, dried over anhydrous sodium sulfate, and evaporated. The residue was recrystallized from ethanol to yield 0.46 g (63% of theory) of 7-ethoxycarbonyl-3-(2-carboxyphenyl)-6,8-dimethyl-4(3H)-quinazolinone melting at 207°–209.5° C.

EXAMPLE 3

A solution of 4 g of 2-amino-5-ethoxycarbonyl-4,6-dimethylbenzoic acid in 40 ml of acetic anhydride was refluxed for 1.5 hours, and then excessive acetic anhydride was removed in vacuo. The residue was recrystallized from ethyl ether to afford 3.8 g (95% of theory) of 6-ethoxycarbonyl-2,5,7,-trimethyl-3,1,4-benzoxazone melting at 118°–119° C.

To a mixture of 2.9 g of the benzoxazone obtained above, 1.22 g of o-toluidine, and 20 ml of toluene was added with stirring a solution of 1.6 g of phosphorous trichloride in 8 ml of toluene. The reaction mixture was refluxed for 3 hours, then cooled, and poured into ice water. The aqueous layer was made alkaline by addition of sodium bicarbonate, and the organic layer was separated. The aqueous layer was extracted with ethyl acetate, and the combined organic extracts were washed with water, and dried over anhydrous sodium sulfate. The solvent was distilled off. The resulting residue was recrystallized from ethanol to yield 4.17 g (84.7% of theory) of 6-ethoxycarbonyl-3-(o-tolyl)-2,5,7-trimethyl-4(3H)-quinazolinone melting at 129°–130° C. $^1$H NMR: $\delta$(CDCl$_3$) 1.44 (t, 3H), 2.14 (s, 3H), 2.45 (s, 3H), 2.75 (s, 3H), 2.94 (s, 3H), 4.50 (q, 2H), 7.35–7.53 (m, 5H).

EXAMPLE 4

To a mixture consisting of 1 g of 2-amino-5-ethoxycarbonyl-4,6-dimethylbenzoic acid, 20 ml of benzene, and 0.7 ml of pyridine in a flask cooled with ice water was added dropwise with stirring a solution of 600 mg of acetyl chloride in 5 ml of benzene. The mixture was further stirred for 5 hours at room temperature, and then heated to reflux for one hour. After cooling, the mixture was shaken with dilute hydrochloric acid and the layers were separated. The acidic aqueous layer was extracted with ethyl acetate, and the combined organic extracts were washed with water, and dried over sodium sulfate. The solvent was removed by distillation. The resulting residue was recrystallized from ethanol/water to yield 1.02 g of 2-acetylamino-5-ethoxycarbonyl-4,6-dimethylbenzoic acid melting at 170°–171° C.

To a room temperature mixture consisting of 1 g of the above acid, 650 mg of o-chloroaniline, and 30 ml of toluene was added with stirring a solution of 0.3 ml of phosphorus trichloride in 10 ml of toluene. The mixture was refluxed for 3 hours, then cooled, and poured into ice water. The aqueous layer was made alkaline by addition of sodium carbonate and the layers were separated. The aqueous layer was extracted with chloroform, and the combined organic extracts were washed with water, and dried over anhydrous sodium sulfate. The solvent was distilled off. The resulting residue was recrystallized from ethanol/water to yield 840 mg (63% of theory) of 3-(2-chlorophenyl)-6-ethoxycarbonyl-2,5,7-trimethyl-4(3H)-quinazolinone melting at 131°–132° C. $^1$H NMR: $\delta$(CDCl$_3$) 1.42 (t, 3H), 2.21 (s, 3H), 2.46 (s, 3H), 2.81 (s, 3H), 4.50 (q, 2H), 7.30–7.85 (m, 5H).

EXAMPLE 5

To a mixture consisting of 1 g of 2-amino-4-ethoxycarbonyl-3,5-dimethylbenzoic acid, 20 ml of dry benzene, and 0.7 ml of pyridine in a flask cooled with ice water was added dropwise with stirring a solution of 450 mg of acetyl chloride in 5 ml of benzene. The reaction mixture was stirred overnight, and then shaken with dilute hydrochloric acid. The layers were separated. The acidic aqueous layer was extracted with ethyl acetate, and the combined organic extracts were washed with water, and dried over sodium sulfate. The solvent was removed by distillation. The residue was recrystallized from ethyl acetate to afford 0.84 g of 2-acetylamino-4-ethoxycarbonyl-3,5-dimethylbenzoic acid melting at 164° C.

To a room temperature mixture consisting of the above acid, 0.38 g of m-chloroaniline, and 30 ml of toluene, was added with stirring a solution of 0.18 ml of phosphorous trichloride in 10 ml of toluene. The mixture was refluxed for 3 hours, then cooled, and poured into ice water. The aqueous layer was made alkaline by addition of saturated aqueous sodium carbonate, and the layers were separated. The aqueous layer was extracted with chloroform, and the combined organic extracts were washed with water and dried over anhydrous sodium sulfate. The solvent was evaporated. The resulting residue was recrystallized from ethanol to yield 0.67 g (60% of theory) of 3-(m-chlorophenyl)-7-ethoxycarbonyl-2,6,8-trimethyl-4(3H)-quinazolinone melting at 150.5°–151.5° C. $^1$H NMR: $\delta$(CDCl$_3$) 1.43 (t, 3H), 2.25 (s, 3H), 2.41 (s, 3H), 2.58 (s, 3H), 4.47 (q, 2H), 7.05–7.53 (m, 4H), 7.91 (s, 1H).

EXAMPLE 6

In an open flask a mixture consisting of 600 mg of methyl 2-amino-5-ethoxycarbonyl-3,5-dimethylbenzoate and 850 ml of N,N-diphenylformamidine was heated to 200° C. with occasional swirling. The temperature of the reaction mixture was maintained at around 200° C. for 1.5 hours. After cooling, the mixture was taken up in ethyl acetate, and the ethyl acetate extract was washed successively with dilute hydrochloric acid and water, and dried over sodium sulfate. The solvent was removed by evaporation. Chromatography on silica gel column and recrystallization from ethanol/water yielded 556 mg (71.9% of theory) of 6-ethoxycarbonyl-5,7-dimethyl-3-phenyl-4(3H)-quinazolinone melting at 102°–103° C. $^1$H NMR: (CDCl$_3$) 1.43 (t, 3H), 2.48 (s, 3H), 2.83 (s, 3H), 4.48 (q, 2H), 7.30–7.90 (m, 6H), 8.14 (s, 1H).

EXAMPLE 7

A mixture consisting of 500 mg of methyl 2-amino-4-ethoxycarbonyl-3,5-dimethylbenzoate and 640 mg of N,N-bis-(o-chlorophenyl)-formamidine was heated to 200° C. with occasional swirling in an open flask. The temperature of the mixture was maintained at around 200° C. for 1.5 hours. After cooling, the mixture was taken up in ethyl acetate, and then, the organic extract was washed with dilute hydrochloric acid, and with water, and dried over anhydrous magnesium sulfate. The solvent was evaporated. The resulting residue was chromatographed on silica gel to give 385 mg (54% of theory) of 3-(2-chlorophenyl)-7-ethoxycarbonyl-6,8-dimethyl-4(3H)-quinazolinone melting at 151°–152° C. (recryst. from ethanol). $^1$H NMR: $\delta$(CDCl$_3$) 1.49 (t, 3H), 2.46 (s, 3H), 2.62 (s, 3H), 4.48 (q, 2H), 7.30–7.70 (m, 4H), 7.93 (s, 1H), 8.06 (s, 1H).

EXAMPLES 8–51

In a similar manner to Examples 1, 3, 4, and 6, starting from 2-amino-6-ethoxycarbonyl-4,6-dimethylbenzoic acid the following compounds of formula (I$_a$) were obtained in a 50–80% yield as shown in Table I.

TABLE I

| No. | R$_4$ | Compound of formula (I$_a$) Q | Melting point (°C.) | Recryst. solvent |
|---|---|---|---|---|
| 8 | H | o-fluorophenyl | 172.5–173 | ethanol/water |
| 9 | H | p-fluorophenyl | 138–139 | " |
| 10 | H | o-chlorophenyl | 124–124.5 | " |
| 11 | H | m-chlorophenyl | 136–137 | " |
| 12 | H | p-chlorophenyl | 131.5–132.5 | ethanol |
| 13 | H | p-bromophenyl | 140–141 | ethanol/water |
| 14 | H | o-tolyl | 90–91 | " |
| 15 | H | m-tolyl | 84–85 | " |
| 16 | H | p-tolyl | 124–124.5 | " |
| 17 | H | p-methoxyphenyl | 126–127 | ethanol |
| 18 | H | 3,4-dimethoxyphenyl | 145–146 | ethanol/water |
| 19 | H | 3,4-methylenedioxyphenyl | 168–169 | " |
| 20 | H | 3,4,5-trimethoxyphenyl | 152–153 | " |
| 21 | H | o-nitrophenyl | 119–120 | ethanol |
| 22 | H | m-nitrophenyl | 156–157 | " |
| 23 | H | p-nitrophenyl | 166–167 | " |
| 24 | H | o-(trifluoromethyl)-phenyl | 123.5–124 | " |
| 25 | H | m-(trifluoromethyl)- | 137–138 | ethanol/water |

TABLE I-continued

Compound of formula (I_a): structure with C₂H₅OOC and CH₃ substituents on benzene ring bearing C(=O)-N(Q)-N=C-R₄

| No. | R₄ | Q | Melting point (°C.) | Recryst. solvent |
|---|---|---|---|---|
| 26 | H | o-cyanophenyl | 167–168.5 | ethanol |
| 27 | H | p-(dimethylamino)phenyl | hydrochloride: 155–156 | ethanol |
| 28 | H | o-(ethoxycarbonyl)phenyl | 158.5–160 | ethanol/water |
| 29 | H | m-(ethoxycarbonyl)phenyl | 105–106 | ethanol |
| 30 | H | p-(ethoxycarbonyl)phenyl | 125.5–129.5 | " |
| 31 | H | o-carboxyphenyl | 178–188 | " |
| 32 | H | p-(ethoxycarbonylmethyl)phenyl | 161–162 | " |
| 33 | H | p-(carboxymethyl)phenyl | 210–211 | " |
| 34 | H | p-acetylphenyl | 166–167 | " |
| 35 | H | 2-methyl-3-pyridyl | 107–109.5 | ethanol/n-hexane |
| 36 | H | 6-methyl-3-pyridyl | 138–140 | ethanol |
| 37 | CH₃ | o-(trifluoromethyl)phenyl | 104–105 | ethanol/ethyl ether |
| 38 | CH₃ | o-(ethoxycarbonyl)phenyl | 123–125 | ethanol/water |
| 39 | CH₃ | o-carboxyphenyl | 189–190 | ethanol/n-hexane |
| 40 | CH₃ | p-(ethoxycarbonylmethyl)phenyl | 144–145 | ethane/n-hexane |
| 41 | CH₃ | p-(carboxymethyl)phenyl | 201–202 | acetone |
| 42 | CH₃ | o-cyanophenyl | 151–152 | ethanol/n-hexane |
| 43 | CH₃ | o-nitrophenyl | 129–129.5 | ethanol |
| 44 | CH₃ | 3,4-dimethoxyphenyl | 70–72 | " |
| 45 | CH₃ | 3,4-methylenedioxyphenyl | 164–165 | ethyl acetate/ether |
| 46 | CH₃ | o-acetylphenyl | 149–150 | ethyl acetate/ether |
| 47 | CH₃ | p-acetylphenyl | 80–81 | ethyl acetate/ether |
| 48 | CH₃ | 4-hydroxy-2-methylphenyl | 202–203 | ethanol/n-hexane |
| 49 | CH₃ | 2-chloro-4-(ethoxycarbonyl)phenyl | 162–163 | ethyl ether |
| 50 | CH₃ | 3-pyridyl | 114–115 | ethanol/n-hexane |
| 51 | CF₃ | o-tolyl | 158–159 | ethanol |

EXAMPLES 52–82

In a similar manner to Examples 2, 5, and 7, starting from 2-amino-4-ethoxycarbonyl-3,5-dimethylbenzoic acid the following compounds of the formula (I_b) were obtained in a 50–80% yield as shown in Table II.

TABLE II

Compound of formula (I_b): structure with CH₃ and C₂H₅OOC substituents on benzene ring bearing C(=O)-N(Q)-N=C-R₄

| No. | R₄ | Q | Melting point (°C.) | Recryst. solvent |
|---|---|---|---|---|
| 52 | H | phenyl | 154–155 | ethyl ether/n-hexane |
| 53 | H | m-fluorophenyl | 148–149 | ethanol |
| 54 | H | m-chlorophenyl | 145–146 | " |
| 55 | H | o-bromophenyl | 155–156 | ethanol/water |
| 56 | H | o-tolyl | 110.5–111.5 | " |
| 57 | H | o-methoxyphenyl | 153–154 | ethanol |
| 58 | H | m-methoxyphenyl | 126–127 | " |
| 59 | H | o-nitrophenyl | 177–178 | " |
| 60 | H | m-cyanophenyl | 168–169 | ethanol/chloroform |
| 61 | H | p-cyanophenyl | 189–190.5 | " |
| 62 | H | p-(ethoxycarbonyl)phenyl | 123–124 | ethanol/water |
| 63 | H | p-hydroxyphenyl | 127–130 | ethanol/n-hexane |
| 64 | H | m-(dimethylamino)phenyl | hydrochloride: 145.5–146.5 | ethanol/ethyl acetate |
| 65 | H | p(dimethylamino)phenyl | hydrochloride: 151–152.5 | ethanol |
| 66 | H | o-(trifluoromethyl)phenyl | 174–175 | ethanol |
| 67 | H | 2-nitro-4-(trifluoromethyl)phenyl | 188–189 | " |
| 68 | H | m-(ethoxycarbonyl)phenyl | 134–135 | " |
| 69 | H | m-(hydroxymethyl)phenyl | 138–138 | ethanol/ethyl ether |
| 70 | CH₃ | o-tolyl | 138.5–139 | ethanol |
| 71 | CH₃ | o-(ethoxycarbonyl)phenyl | 129–130 | ethanol/water |
| 72 | CH₃ | p-(ethoxycarbonyl)phenyl | 153–154 | ethanol |
| 73 | CH₃ | p-carboxyphenyl | 228–230 | " |
| 74 | CH₃ | m-hydroxyphenyl | 133–135 | ethyl ether |
| 75 | CH₃ | p-(hydroxymethyl)phenyl | 160–161 | ethanol |
| 76 | CH₃ | 2,6-dichlorophenyl | 178–179 | ethanol/water |
| 77 | CH₃ | p-(dimethylamino)phenyl | hydrochloride: 206–208 | ethanol |
| 78 | CH₃ | o-chlorophenyl | 154.5–155.5 | ethanol/n-hexane |
| 79 | CH₃ | o-nitrophenyl | 178.5–179.5 | ethanol |
| 80 | CH₃ | o-(trifluoromethyl)phenyl | 132–133 | " |
| 81 | CH₃ | 3-chloro-2-methylphenyl | 189.5–190 | " |
| 82 | CH₃ | p-acetylphenyl | 185–186 | ethanol/water |
| 83 | CH₃ | o-(dimethylaminomethyl)phenyl | 153–155 | HCl: 153–155 ethanol/ether |

EXAMPLE 84

To an ice-cooled mixture consisting of 500 mg of 2-amino-5-ethoxycarbonyl-4,6-dimethylbenzoic acid, 15 ml of benzene, and 0.3 ml of pyridine was added dropwise with stirring a solution of 323 mg of isobutyryl chloride in 2 ml of benzene. After completion of the addition, the reaction mixture was further stirred for 5 hours at room temperature, and then heated to reflux for one hour. After cooling, the mixture was shaken with dilute hydrochloric acid and the layers were separated. The slightly acidic aqueous layer was extracted with ethyl acetate, and the combined organic extracts were washed with water, dried over anhydrous sodium sulfate, and evaporated. The resulting residue was recrystallized from ethyl ether/n-hexane to yield 523 mg of 5-ethoxycarbonyl-2-isobutyrylamino-4,6-dimethylbenzoic acid.

To a mixture consisting of 400 mg of the above acid, 320 mg of o-chloroaniline, and 20 ml of toluene was added with stirring a solution of 179 mg of phosphorous trichloride in 5 ml of toluene at room temperature. The mixture was refluxed for 3 hours, then cooled, and poured into ice water. The aqueous layer was made alkaline by addition of sodium bicarbonate, and then the toluene layer was separated. The aqueous layer was extracted with ethyl acetate, and the combined organic extracts were washed with water, dried over anhydrous sodium sulfate, and evaporated. The residue was chromatographed on silica gel column. Elution with benzene/chloroform (10:1, v/v) and recrystallization from ethanol afforded 180 mg (34.7% of theory) of 6-ethoxycarbonyl-2-isopropyl-3-(2-chlorophenyl)-5,7-dimethyl-4(3H)-quinazolinone melting at 115°–116° C. $^1$H NMR: $\delta$(CDCl$_3$) 1.23 (d, 2H), 1.34 (d, 2H), 1.43 (t, 3H), 2.13–2.70 (m, 1H), 2.45 (s, 3H), 2.81 (s, 3H), 4.49 (q, 2H), 7.25–7.80 (m, 5H)

EXAMPLES 85–87

In a similar manner to Example 83, using the following acyl chlorides instead of isobutyryl chloride, the following quinazolinone derivative were obtained in a 30–50% yield.

| No. | Acyl chloride | Product | Melting point (recryst. solvent) |
|---|---|---|---|
| 85 | n-propionyl chloride | 3-(2-chlorophenyl)-6-ethoxycarbonyl-2-ethyl-5,7-dimethyl-4(3H)-quinazolinone | 104–105° C. ethanol/n-hexane |
| 86 | n-butyryl chloride | 3-(2-chlorophenyl)-6-ethoxycarbonyl-5,7-dimethyl-2-n-propyl-4(3H)-quinazolinone | 88–89° C. ethanol |
| 87 | n-hexanoyl chloride | 2-n-amyl-3-(2-chlorophenyl)-6-ethoxycarbonyl-5,7-dimethyl-4(3H)-quinazolinone | 79–80° C. ethanol |

EXAMPLE 88

To an ice-cooled mixture consisting of 0.8 g of 2-amino-5-ethoxycarbonyl-4,6-dimethylbenzoic acid, 20 ml of dry benzene, and 0.5 ml of pyridine was added dropwise with stirring a solution of 0.4 ml of chloroacetyl chloride in 5 ml of benzene. The mixture was stirred overnight and then, shaken with dilute hydrochloric acid. The layers were separated. The aqueous layer was extracted with ethyl acetate, and the combined organic extracts were washed with water, dried over sodium sulfate, and evaporated. The residue was recrystallized from ethyl ether/n-hexane to give 0.65 g of 2-chloroacetylamino-5-ethoxycarbonyl-4,6-dimethylbenzoic acid (m.p. 124°–125° C.).

To a mixture consisting of 0.65 g of the above acid, 0.5 g of o-chloroaniline, and 30 ml of toluene was added with stirring a solution of 0.5 g of phosphorous trichloride in 10 ml of toluene. The reaction mixture was refluxed gently for 3 hours, then cooled, and poured into ice water. The aqueous layer was made alkaline by addition of saturated aqueous sodium bicarbonate, and the layers were separated. The aqueous layer was extracted with ethyl acetate, and the combined organic extracts were washed with water, dried over sodium sulfate, and evaporated. The residue was chromatographed on silica gel column. Elution with benzene/chloroform (5:1, v/v) and recrystallization from ethyl ether/n-hexane afforded 0.45 g of 2-chloromethyl-3-(2-chlorophenyl)-2-ethoxycarbonyl-5,7-dimethyl-4(3H)-quinazolinone melting at 94°–95° C.

A mixture of 0.45 g of the above quinazolinone, 0.5 g of anhydrous sodium acetate, and 20 ml of ethanol was refluxed for 5 hours and then, concentrated under reduced pressure. The resulting concentrate was diluted with water and extracted with ethyl acetate. The ethyl acetate extract was washed with water, dried over anhydrous magnesium sulfate, and evaporated. The residue was dried in vacuo and dissolved in 10 ml of absolute ethanol. To the solution was added a solution of 10 mg of sodium metal in 1 ml of absolute ethanol. The mixture was stirred for 5 hours at room temperature, and then neutralized by addition of Dowex-50W-X8. The resin was filtered, and the filtrate was evaporated under reduced pressure. The residue so obtained was recyrstallized from ethyl ether/n-hexane to yield 0.42 g of 3-(2-chlorophenyl)-6-ethoxycarbonyl-2-hydroxymethyl-5,7-dimethyl-4(3H)-quinazolinone melting at 151°–152° C. $^1$H NMR: $\delta$(CDCl$_3$) 1.48 (t, 3H), 2.52 (s, 3H), 2.88 (s, 3H), 4.19 (s, 2H), 4.20 (b, 1H), 4.63 (q, 2H), 7.52–7.81 (m, 5H)

EXAMPLES 89–91

In a similar manner to Example 87 the following quinazolinone derivative were obtained.

No. 89
6-ethoxycarbonyl-2-hydroxymethyl-5,7-dimethyl-3-(o-tolyl)-4(3H)-quinazolinone: m.p. 130.5°–131.5° C. (recryst. from ethanol/n-hexane)

No. 90
6-ethoxycarbonyl-2-hydroxymethyl-5,7-dimethyl-3-(3,4-dimethoxyphenyl)-4(3H)-quinazolinone: m.p. 181°–182° C. (recryst. from ethanol/n-hexane)

No. 91
6-ethoxycarbonyl-2-hydroxymethyl-5,7-dimethyl-3-(3,4-methylenedioxyphenyl)-4(3H)-quinazolinone: m.p. 159°–161° C. (recryst. from ethanol/n-hexane)

EXAMPLE 92

6-Ethoxycarbonyl-2,5,7-trimethyl-3-(o-nitrophenyl)-4(3H)-quinazolinone (the compound of Example No. 43) was reduced with Raney Nickel in hydrogen atmosphere in the presence of hydrazine hydrate to give 3-(o-aminophenyl)-6-ethoxycarbonyl-2,5,7-trimethyl-4(3H)-quinazolinone, monohydrochloride of which melted at 168°–169.5° C. (recrystallized from ethanol/ether).

Test for blood vessel relaxing effect

Albino rabbits weighing 2.5 to 3 kg were sacrificed by exsanguination. The thoracic aorta, superior mesenteric artery, and basilar artery were quickly excised. The arteries were detached from fats and connective tissues and then, cut at an angle of approximately 45° to the longitudinal axis into strips. The width and length of the strips were 2.5 mm and 30 mm in the case of aorta, 2 mm and 25 mm in mesenteric artery, and 1 mm and 20 mm in basilar artery, respectively. Each experiment was carried out in a conventional tissue bath. The composition of the bathing solution was as follows (in millimolar concentrations): NaCl, 115.0; KCl, 4.7; CaCl$_2$. 2H$_2$O, 2.5; MgCl$_2$.6H$_2$O, 1.2; NaHCO$_3$, 25; KH$_2$PO$_4$, 1.2; and glucose 10.0. The tissue bath solutions were maintained at 37°, and bubbled with a mixture of 95% O$_2$ and 5% CO$_2$. The upper end of the strip was connected to the lever of a force-displacement transducer by a silk thread. Initial resting tensions of 1.5 g, 1 g, and 0.5 g were applied to the aorta, mesenteric and basilar artery, respectively.

Before the experiments commenced, preparations were equilibrated for 2 hours in the bathing solution. During the equilibration period, the solutions were replaced every 30 minutes with fresh media. After equilibration the strip was constricted by addition of potassium chloride in a concentration of 20 mM in the case of aorta and 25 mM in mesenteric and basilar artery. After the constriction induced by potassium chloride reached a maximum, a solution of test compound in dimethylsulfoxide was added to the bath in the concentration indicated in Table III, and the resulting relaxation was recorded. The concentration of the dimethylsulfoxide did not exceed 0.3%. At the end of each series of experiments, papaverine was added to the bath in a concentration of $3 \times 10^{-4}$ M in the case of aorta and $1 \times 10^{-4}$ M in mesenteric and basilar artery, and relaxation induced by papaverine was taken as 100%. The relaxing effects of test compounds shown in Table III were expressed as percentages against the maximum relaxation induced papaverine. Each compound was tested three times and the relaxation effect was a mean value obtained from the three experiments.

TABLE III

| Blood vessel Concentration | Relaxing effect (%) | | |
| --- | --- | --- | --- |
| | Thoracic aorta $3 \times 10^{-5}$ M | Mesenteric artery $3 \times 10^{-6}$ M | Basilar artery $3 \times 10^{-6}$ M |
| Test Compound | | | |
| Papaverine (control) | 52 ± 2.1 | 42 ± 5.0 | 21 ± 3.3 |
| Methagalone | 5 ± 3.6 | NT | NT |
| 7-Ethoxycarbonyl-6,8-dimethyl-4-hydroxymethyl-1-phthalazone | 19 ± 1.2 | NT | NT |
| 7-Ethoxycarbonyl-6,8-dimethyl-1-phthalazone | 0 | 0 | 0 |
| The compounds of the present invention | | | |
| Compound of No. 14 | 42 ± 6.2 | 2 ± 2.8 | 25 ± 3.8 |
| Compound of No. 10 | 51 ± 7.0 | 29 ± 3.7 | 57 ± 14.9 |
| Compound of No. 24 | 30 ± 4.4 | 37 ± 18.7 | 51 ± 12.3 |
| Compound of No. 21 | 31 ± 3.9 | 7 ± 5.7 | 44 ± 9.0 |
| Compound of No. 3 | 47 ± 6.4 | 9 ± 12.9 | 49 ± 10.2 |
| Compound of No. 4 | 68 ± 7.5 | 41 ± 6.7 | 62 ± 9.6 |
| Compound of No. 37 | 61 ± 7.5 | 24 ± 8.2 | 80 ± 9.6 |
| Compound of No. 43 | 64 ± 10.3 | 37 ± 5.7 | 70 ± 14.4 |

NT = not tested

Test for acute toxicity

A suspension of test compound in 0.5% CMC aqueous solution containing Tween 80 was orally administered to mice, and during the following 8 days the number of dead mice was counted. The result is shown below.

| Test compound | Dose | number of dead mice / number of tested mice |
| --- | --- | --- |
| Compound of No. 14 | 300 mg/kg | 0/6 |
| Compound of No. 10 | 300 mg/kg | 0/6 |
| Compound of No. 24 | 300 mg/kg | 0/6 |
| Compound of No. 21 | 300 mg/kg | 0/6 |
| Compound of No. 3 | 300 mg/kg | 0/6 |
| Compound of No. 4 | 300 mg/kg | 0.6 |
| Compound of No. 37 | 300 mg/kg | 0/6 |
| Compound of No. 43 | 300 mg/kg | 0/6 |

What we claim is:

1. A compound of the formula

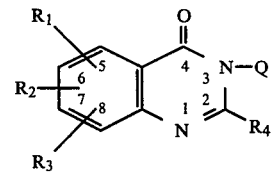

wherein

R$_1$ and R$_3$ represent lower alkyl and R$_2$ represents linear or branched lower alkoxycarbonyl in which R$_1$, R$_2$ and R$_3$ are located at the 5-, 6- and 7-positions or at the 6-, 7- and 8-positions in this order;

R$_4$ represents a member selected from the group consisting of hydrogen, linear or branched alkyl, monohalogenomethyl, trihalogenomethyl, acetoxymethyl and hydroxymethyl;

Q represents a group of the formula

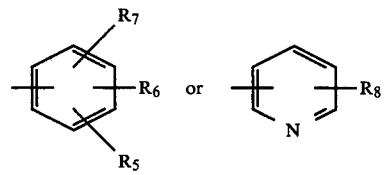

in which

R$_5$ represents a member selected from the group consisting of hydrogen, halogen, lower alkyl and lower alkoxy, R$_6$ represents a member selected from the group consisting of hydrogen, halogen, lower alkyl, lower alkoxy, a trifluoromethyl and nitro, R$_5$ and R$_6$ may together represent methylenedioxy when they are located on adjacent carbon atoms on the nucleus, R$_7$ represents a member selected from the group consisting of hydrogen, halogen, lower alkyl, lower alkoxy, trifluoromethyl, nitro, cyano, hydroxyl, lower alkanoyl, carboxyl, lower alkoxycarbonyl, hydroxymethyl, carboxymethyl, lower alkoxycarbonylmethyl, amino, di-lower alkylamino, and (di-lower alkylamino) lower alkyl, and R$_8$ represents hydrogen or lower alkyl; and when R$_4$ represents methyl, and when R$_1$, R$_2$ and R$_3$ are located at the 6-, 7- and 8-positions in this order and R$_4$ represents hydroxymethyl, R$_5$, R$_6$ and R$_7$ do not simultaneously represent hydrogen; or its pharmaceutically acceptable acid addition salt.

2. The compound of claim 1, wherein said compound is 3-(o-chlorophenyl)-6-ethoxycarbonyl-2,5,7-trimethyl-4(3H)-quinazolinone.

3. The compound of claim 1, wherein said compound is 6-ethoxycarbonyl-3-[o-(trifluoromethyl)phenyl]-2,5,7-trimethyl-4(3H)-quinazolinone.

4. The compound of claim 1, wherein said compound is 6-ethoxycarbonyl-2,5,7-trimethyl-3-(o-nitrophenyl)-4(3H)-quinazolinone.

5. The compound of claim 1, wherein said compound is 3-(o-chlorophenyl)-6-ethoxycarbonyl-5,7-dimethyl-4(3H)-quinazolinone.

6. The compound of claim 1, wherein said compound is 6-ethoxycarbonyl-3-[o-(trifluoromethyl)phenyl]-5,7-dimethyl-4(3H)-quinazolinone.

7. The compound of claim 1, wherein said compound is 6-ethoxycarbonyl-5,7-dimethyl-3-(o-nitrophenyl)-4(3H)-quinazolinone.

8. The compound of claim 1 wherein $R_1$, $R_3$ represent an alkyl of 1 to 4 carbon atoms and $R_2$ represents linear or branched alkoxycarbonyl of 1 to 4 carbon atoms in the alkoxy group moiety;

$R_4$ represents a member selected from the group consisting hydrogen, linear or branched alkyl of 1 to 6 carbon atoms, monohalogenomethyl, trihalogenomethyl, acetoxymethyl and hydroxymethyl;

$R_5$ represents a member selected from the group consisting of hydrogen, halogen, alkyl of 1 to 4 carbon atoms and alkoxy of 1 to 4 carbon atoms, $R_6$ represents a member selected from the group consisting of hydrogen, halogen, alkyl of 1 to 4 carbon atoms, alkoxy of 1 to 4 carbon atoms, trifluoromethyl and nitro, and $R_5$ and $R_6$ may together represent methylenedioxy when they are located on adjacent carbon atoms of the nucleus, $R_7$ represents a member selected from the group consisting of hydrogen, halogen, alkyl of 1 to 4 carbon atoms, alkoxy of 1 to 4 carbon atoms, trifluoromethyl, nitro, cyano, hydroxyl, alkanoyl of 1 to 4 carbon atoms, carboxyl, alkoxycarbonyl of 1 to 4 carbon atoms in the alkoxy moiety, hydroxymethyl, carboxymethyl, alkoxycarbonylmethyl of 1 to 4 carbon atoms in the alkoxy moiety, amino, di-alkylamino of 1 to 4 carbon atoms in the alkyl moiety, and [di-($C_1$–$C_3$ alkyl)amino] ($C_1$–$C_4$)alkyl, and $R_8$ represents hydrogen or alkyl of 1 to 4 carbon atoms; and when $R_4$ represents methyl and when $R_1$, $R_2$ and $R_3$ are located at the 6-, 7- and 8-positions in this order and $R_4$ is hydroxymethyl, $R_5$, $R_6$ and $R_7$ do not simultaneously represent hydrogen.

9. The compound of claim 1 wherein $R_1$ and $R_3$ are each methyl, $R_2$ is ethoxycarbonyl and $R_4$ is hydrogen.

10. The compound of claim 1 wherein $R_1$ and $R_3$ are each methyl, $R_2$ is ethoxycarbonyl and $R_4$ is a linear or branched alkyl of 1 to 6 carbon atoms.

11. The compound of claim 1 wherein $R_1$ and $R_3$ are each methyl, $R_2$ is ethoxycarbonyl and $R_4$ is hydroxymethyl.

12. The compound of any one of claims 9, 13, or 14 wherein Q represents a radical selected from the group consisting of (2-hydroxyphenyl), (ethoxycarbonyl)phenyl, tolyl, halophenyl, phenyl, p-methoxyphenyl, 3,4-dimethoxyphenyl, 3,4-methylenedioxyphenyl, 3,4,5-trimethoxyphenyl, nitrophenyl, (trifluoromethyl)phenyl, cyanophenyl, (dimethylamino)phenyl, carboxyphenyl, (carboxymethyl)phenyl, acetylphenyl, 4-hydroxy-2-methylphenyl, 2-chloro-4-(ethoxycarbonyl)phenyl, hydroxyphenyl, (dimethylamino)phenyl, 2-nitro-4-(trifluoromethyl)phenyl, (hydroxymethyl)phenyl, 2,6-dichlorophenyl, 3-chloro-2-methylphenyl and (dimethylaminomethyl)phenyl.

13. The compound of claim 1 wherein Q represents the group of the formula

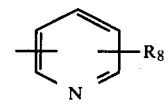

14. A vasodilating, hypotensive and antiatherosclerotic pharmaceutical composition comprising a pharmaceutically effective amount of a compound selected from 3-aromatic moiety substituted-4-quinazolinones and their pharmaceutically acceptable acid addition salts and a pharmaceutically acceptable diluent or carrier, said quinazolinone compounds being of the formula

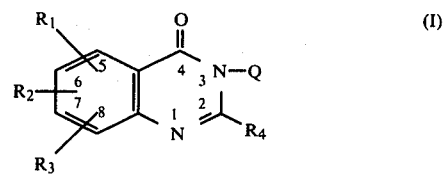

wherein $R_1$ and $R_3$ represent lower alkyl and $R_2$ represents linear or branched lower alkoxycarbonyl in which $R_1$, $R_2$ and $R_3$ are located at the 5-, 6- and 7-positions or at the 6-, 7- and 8-positions in this order;

$R_4$ represents a member selected from the group consisting of hydrogen, linear or branched alkyl, monohalogenomethyl, trihalogenomethyl, acetoxymethyl and hydroxymethyl;

Q represents a group of the formula

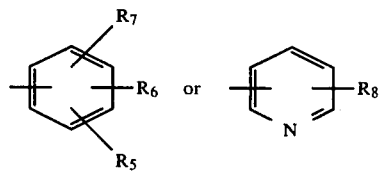

in which $R_5$ represents a member selected from the group consisting of hydrogen, halogen, lower alkyl and lower alkoxy, $R_6$ represents a member selected from the group consisting of hydrogen, halogen, lower alkyl, lower alkoxy, trifluoromethyl and nitro, $R_5$ and $R_6$ may together represent methylenedioxy when they are located on adjacent carbon atoms on the nucleus, $R_7$ represents a member selected from the group consisting of hydrogen, halogen, lower alkyl, lower alkoxy, trifluoromethyl, nitro, cyano, lower alkoxycarbonyl, hydroxymethyl, carboxymethyl, lower alkoxycarbonylmethyl, amino, di-lower alkylamino, and (di-lower alkylamino) lower alkyl, and $R_8$ represents hydrogen or lower alkyl; and when $R_4$ represents methyl, and when $R_1$, $R_2$ and $R_3$ are located at the 6-, 7- and 8-positions in this order and $R_4$ represents hydroxymethyl, $R_5$, $R_6$ and $R_7$ do not simultaneously represent hydrogen.

* * * * *